(12) United States Patent
Lipscombe et al.

(10) Patent No.: US 7,237,770 B2
(45) Date of Patent: *Jul. 3, 2007

(54) HUMIDIFIER FOR BREATHABLE GAS APPARATUS

(75) Inventors: Matthew Lipscombe, Camperdown (AU); Richard L. Jones, Hornsby Heights (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 10/872,402

(22) Filed: Jun. 22, 2004

(65) Prior Publication Data

US 2004/0226560 A1    Nov. 18, 2004

Related U.S. Application Data

(60) Division of application No. 10/387,534, filed on Mar. 14, 2003, now Pat. No. 6,772,999, which is a continuation of application No. 09/689,775, filed on Oct. 13, 2000, now Pat. No. 6,554,260.

(30) Foreign Application Priority Data

Oct. 13, 1999    (AU) ..................... PQ3390

(51) Int. Cl.
*B01F 3/04*    (2006.01)

(52) U.S. Cl. .......... 261/142; 261/30; 261/38; 261/63; 261/119.1; 96/371; 128/203.25; 128/203.27; 128/204.14

(58) Field of Classification Search ........ 261/30, 261/38, 63, 119.1, 127, 131, 142, DIG. 29; 128/203.17, 203.25, 203.27, 204.14; 96/364, 96/371

See application file for complete search history.

(56) References Cited

U.S. PATENT DOCUMENTS 1,129,171 A    2/1915    Cunningham (Continued)

FOREIGN PATENT DOCUMENTS

EP    0 8450277 A2    6/1998

(Continued)

OTHER PUBLICATIONS

Product Brochure for "Sullivan® HumidAire™," ResMed Limited © 2001, 4 pages.

*Primary Examiner*—Scott Bushey
(74) *Attorney, Agent, or Firm*—Nixon & Vanderhye P.C.

(57)    ABSTRACT

A humidifier for use with a breathable gas supply apparatus includes a hollow body adapted for partial filling with water to a predetermined maximum water level, a gas inlet to the body above the maximum water level and a gas outlet from the body above the maximum water level. The humidifier further includes a temperature heating element for heating the water and/or an adjustable flow divider adapted to divide the interior of the body above the maximum water level into a relatively dry gas region and a relatively wet gas region. The position of the divider is variable so as to vary the relative proportion of the gas flowing from the inlet to the outlet that passes through the relatively dry and relatively wet gas regions to thereby vary the amount of humidification thereof.

30 Claims, 14 Drawing Sheets

U.S. PATENT DOCUMENTS

| | | |
|---|---|---|
| 2,013,270 A | 9/1935 | Grady |
| 2,535,516 A | 12/1950 | Resek |
| 2,941,528 A | 6/1960 | Fabian et al. |
| 3,424,231 A * | 1/1969 | Truhan ................. 165/230 |
| 3,588,057 A | 6/1971 | Breiling |
| 3,661,368 A | 5/1972 | Metivier |
| 3,715,867 A | 2/1973 | Aoi |
| 3,806,102 A | 4/1974 | Valenta et al. |
| 3,954,920 A | 5/1976 | Heath |
| 4,203,027 A | 5/1980 | O'Hare et al. |
| 4,216,176 A | 8/1980 | Tanaka |
| 4,621,632 A | 11/1986 | Bartels et al. |
| 4,741,871 A | 5/1988 | Payha |
| 4,944,310 A | 7/1990 | Sullivan |
| 5,168,866 A | 12/1992 | Montgomery |
| 5,231,979 A | 8/1993 | Rose et al. |
| 5,245,995 A | 9/1993 | Sullivan et al. |
| 5,537,997 A | 7/1996 | Mechlenburg |
| 5,564,415 A | 10/1996 | Dobson et al. |
| 5,598,837 A | 2/1997 | Sirianne, Jr. et al. |
| 5,992,413 A * | 11/1999 | Martin, Jr. et al. ..... 128/201.13 |
| D419,658 S | 1/2000 | Matchett et al. |
| 6,105,576 A * | 8/2000 | Clawson et al. ........ 128/205.12 |
| 6,135,432 A | 10/2000 | Hebblewhite et al. |
| 6,189,870 B1 | 2/2001 | Withall |
| 6,248,155 B1 | 6/2001 | Seaman |
| 6,338,473 B1 | 1/2002 | Hebblewhite et al. |
| 6,363,930 B1 * | 4/2002 | Clawson et al. ........ 128/201.13 |
| 6,435,180 B1 * | 8/2002 | Hewson et al. ........ 128/204.18 |
| 6,554,260 B1 | 4/2003 | Lipscombe et al. |
| 6,772,999 B2 * | 8/2004 | Lipscombe et al. ......... 261/131 |
| 2003/0132535 A1 | 7/2003 | Lipscombe et al. |

FOREIGN PATENT DOCUMENTS

| | | |
|---|---|---|
| WO | PCT/AU97/00631 | 9/1997 |

* cited by examiner

HUMIDIFIER FOR BREATHABLE GAS APPARATUS

CROSS REFERENCE TO RELATED APPLICATIONS

This application is a divisional of U.S. application Ser. No. 10/387,534, now U.S. Pat. No. 6,772,999, filed Mar. 14, 2003, which is a continuation of U.S. application Ser. No. 09/689,775, now U.S. Pat. No. 6,554,260, filed Oct. 13, 2000, which claims priority to Australian Application No. PQ3390 filed Oct. 13, 1999, the contents of which are incorporated herein by reference in their entireties.

FIELD OF THE INVENTION

The present invention relates to a humidifier.

The invention has been developed primarily for use with a breathable gas supply apparatus in Continuous Positive Airway Pressure (CPAP) treatment of, for example, Obstructive Sleep Apnea (OSA) and other ventilatory assistance treatments such as Non Invasive Positive Pressure Ventilation (NIPPV) and will be described hereinafter with reference to these applications. However, it will be appreciated that the invention is not limited to these particular fields of use and also finds application in, for example, assisted respiration, mechanical ventilation and the like.

BACKGROUND OF THE INVENTION

CPAP treatment is a common ameliorative treatment for breathing disorders including OSA. CPAP treatment, as described in U.S. Pat. No. 4,944,310, provides pressurised air or other breathable gas to the entrance of a patient's airways at a pressure elevated above atmospheric pressure, typically in the range 4–20 cm $H_2O$.

It is also known for the level of treatment pressure to vary during a period of treatment in accordance with patient need, that form of CPAP being known as automatically adjusting nasal CPAP treatment, as described in U.S. Pat. No. 5,245,995.

NIPPV is another form of treatment for breathing disorders which can involve a relatively higher pressure of gas being provided in the patient mask during the inspiratory phase of respiration and a relatively lower pressure or atmospheric pressure being provided in the patient mask during the expiratory phase of respiration.

In other NIPPV modes the pressure can be made to vary in a complex manner throughout the respiratory cycle. For example, the pressure at the mask during inspiration or expiration can be varied through the period of treatment, as disclosed in the applicant's international PCT patent application No. PCT/AU97/00631.

Typically, the ventilatory assistance for CPAP or NIPPV treatment is delivered to the patient by way of a nasal mask. Alternatively, a mouth mask or full face mask or nasal prongs can be used. In this specification any reference to a mask is to be understood as incorporating a reference to a nasal mask, mouth mask, full face mask or nasal prongs.

In this specification any reference to CPAP treatment is to be understood as embracing all of the above described forms of ventilatory treatment or assistance.

Breathable gas supply apparatus broadly comprise a flow generator constituted by a continuous source of air or other breathable gas generally in the form of a blower or driven by an electric motor. The electric motor driving the blower is typically controlled by a servo-controller under the control of a micro controller unit. A hospital piped supply can also be used. The gas supply is connected to a conduit or tube, which in turn is connected to a patient mask which incorporates, or has in close proximity, an exhaust to atmosphere for venting exhaled gases.

In order to prevent drying of the patient's airways during use of a breathable gas supply apparatus it is known to pass the gas through a humidifier-before supplying the gas to the patient. Humidification is achieved by passing the air over a water surface within a humidifier so that the gas absorbs moisture from the water before being delivered to the patient. The two main types of humidifier are passive, where the water is not heated, and active, where the water is heated.

A known passive humidifier is the applicant's Passover (Trade Mark) humidifier. Other passive humidifiers are disclosed in U.S. Pat. Nos. 5,231,979, 5,537,997 and 5,598,837.

A known active humidifier is the applicant's HumidAire (Trade Mark) which heats the water in the humidifier via a thermostatically controlled electric heating element. The temperature of the water is set manually by the patient. The HumidAire humidifier also has a built in safety feature to prevent the heater element reaching excessive temperatures under fault conditions.

European patent application No. EP 0845277 discloses an active humidifier that includes a thermostatically controlled electric heating plate. Active humidifiers are also disclosed in U.S. Pat. Nos. 4,621,632 and 4,203,027.

A disadvantage of known active humidifiers is the expense of the heating elements and associated thermostatic temperature control equipment.

A disadvantage of known passive humidifiers is an inability to easily vary the amount of humidification of the gas.

It is an object of the present invention to substantially overcome or at least ameliorate one or more of the above disadvantages.

SUMMARY OF THE INVENTION

Accordingly, in a first aspect, the present invention provides a humidifier for use with a breathable gas supply apparatus, said humidifier comprising:

a hollow body adapted for partial filling with water up to a predetermined maximum water level;

a gas inlet to the body above the maximum water level;

a gas outlet from the body above the maximum water level; and a constant temperature heating element for heating the water.

In one embodiment, the heating element is disposed within the body.

In another embodiment, the heating element is disposed external the body.

In a second aspect, the present invention provides a humidifier for use with a breathable gas supply apparatus, said humidifier comprising:

a hollow body adapted for partial filling with water to a predetermined maximum water level;

a gas inlet to the body above the maximum water level;

a gas outlet from the body above the maximum water level;

means to heat the water, in the body; and an adjustable flow divider adapted to divide the interior of the body above the maximum water level into a relatively dry gas region and a relatively wet gas region, wherein the position of the divider is variable so as to vary the relative proportion of the gas flowing from the inlet to the outlet that passes through the relatively dry and relatively wet gas regions to thereby vary the amount of humidification thereof.

Preferably, the position of the divider is variable between a first position in which all of the gas is diverted to the relatively wet gas region for maximum humidification, and a second position in which all of the gas is diverted to the relatively dry gas region for minimum humidification.

The heating means is preferably a constant temperature heating element, such as a self regulating wire.

The humidifier desirably also includes a storage reservoir adapted to replenish the water in the body.

The divider preferably also includes baffle plates. The position of the baffle plates can be fixed or adjustable.

In one embodiment, the divider is a generally planar plate of substantially complimentary cross section to the interior of the body above the maximum water level. The plate preferably includes a threaded hole adapted to engage a threaded rod, wherein rotation of the rod causes the plate to move between the first and second positions. The exterior of the plate preferably forms a substantially fluid-tight seal with the interior of the body.

In another embodiment, the divider includes a first end remote the gas inlet and the gas outlet and a second end adjacent the gas inlet and the gas outlet, wherein the divider is adapted to rotate about or near the first end to cause the second end to move between the first and second positions.

In a further embodiment, the divider includes a first and second end adjacent the gas inlet and the gas outlet, wherein the divider is adapted to rotate about or near its centre to cause the first and second ends to move between the first and second positions.

In a third aspect, the present invention provides a humidifier for use with a breathable gas supply apparatus, said humidifier comprising:

a hollow body adapted for partial filling with water to a predetermined maximum water level;

a gas inlet to the body above the maximum water level;

a gas outlet from the body above the maximum water level;

a constant temperature heating element for heating the water; and an adjustable flow divider adapted to divide the interior of the body above the maximum water level into a relatively dry gas region and a relatively wet gas region, wherein the position of the divider is variable so as to vary the relative proportion of the gas flowing from the inlet to the outlet that passes through the relatively dry and relatively wet gas regions-to thereby vary the amount of humidification thereof.

BRIEF DESCRIPTION OF THE DRAWINGS

Preferred embodiments of the invention will now be described, by way of examples only, with reference to the accompanying drawings in which.

DETAILED DESCRIPTION OF THE PREFERRED EMBODIMENTS

Figure 1:
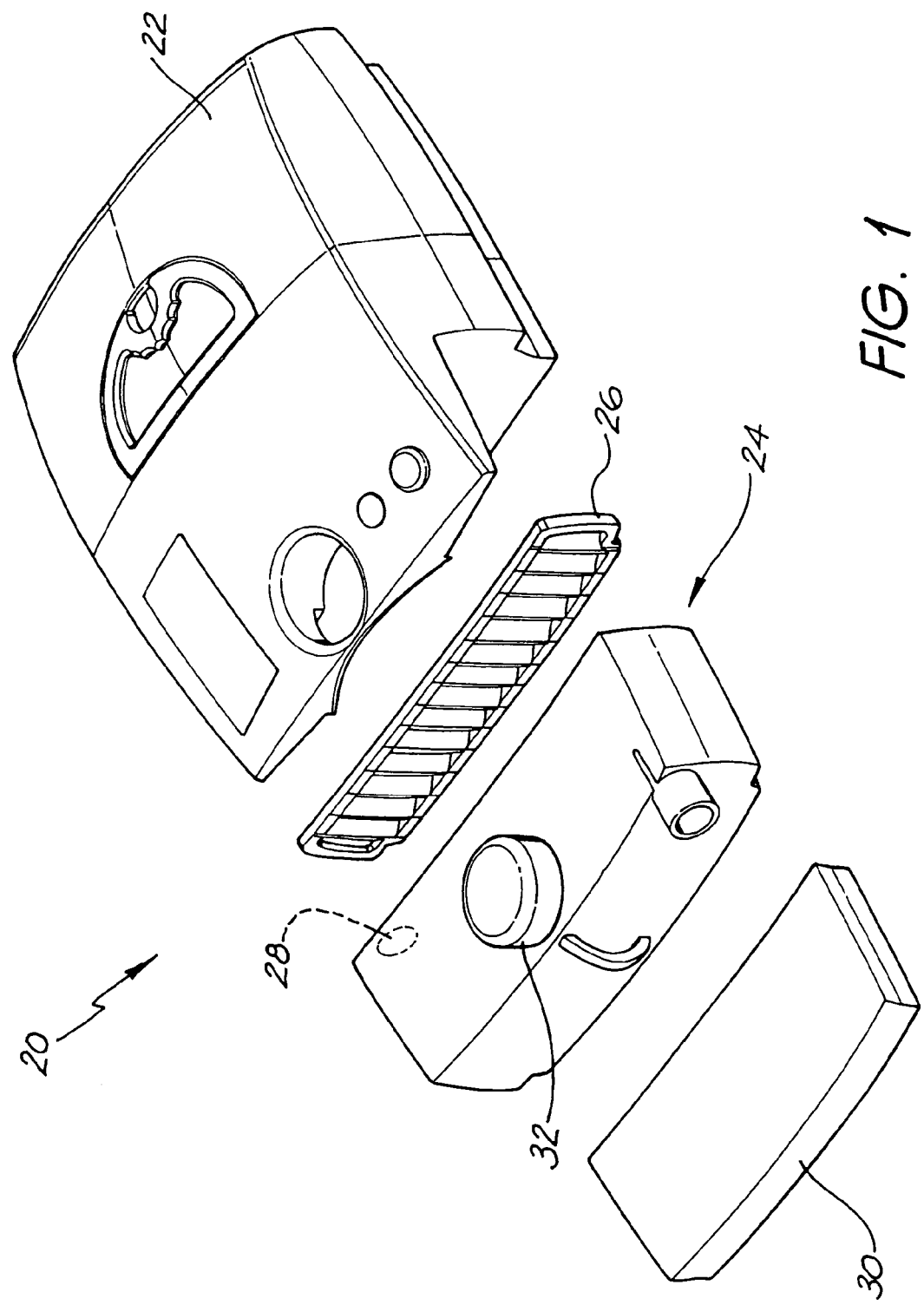
FIG. 1 is an exploded perspective view of a humidifier according to a first embodiment of the invention.

FIG. 1 is an exploded view of a breathable gas supply apparatus 20 which comprises a flow generator 22, a first embodiment of a humidifier 24 according to the invention, an anti-bacterial filter 26 and a heating element 30. The filter 26 is operatively positioned between the outlet of the flow generator 22 (not shown) and the inlet 28 of the humidifier 24. In another embodiment (not shown), the filter is operatively positioned between the outlet of the humidifier and the patient. In the latter, the filter reduces the transfer of bacteria from the patient to the humidifier, and vice-versa.

The humidifier 24 includes a control knob 32 which can be rotated in order to vary the amount of humidification of the gas flowing through the humidifier between a maximum and minimum amount. The components of the humidifier 24 which permit this adjustable humidification will be more completely described with reference to the embodiments of the invention shown in FIGS. 2 to 9, 11, 12, 13, 14, 15, 16 and 17.

The heating element 30 is of self regulating, constant temperature type. The heating element 30 advantageously simplifies the humidifier and breathable gas supply apparatus overall by obviating the need for thermostatic temperature control equipment.

The heating element 30 is positioned external and under the humidifier. In another embodiment (not shown), the heating element is suitably insulated and/or water proofed and positioned inside the body of the humidifier.

Figure 2:
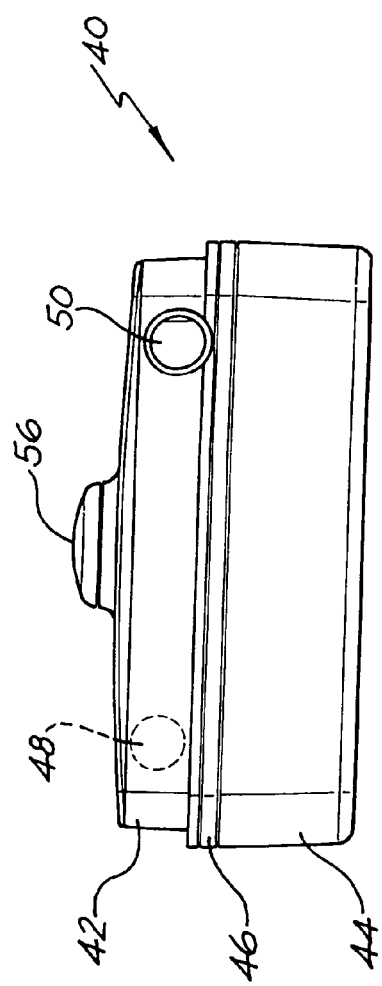
FIG. 2 is a front view of a humidifier according to a second embodiment of the invention.
Figure 4:
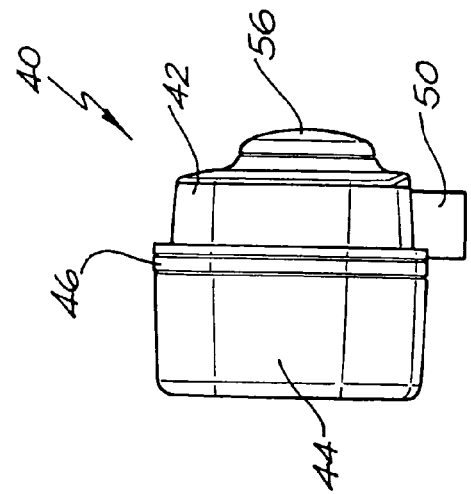
FIG. 4 is a side view of the humidifier shown in FIG. 2.
Figure 3:
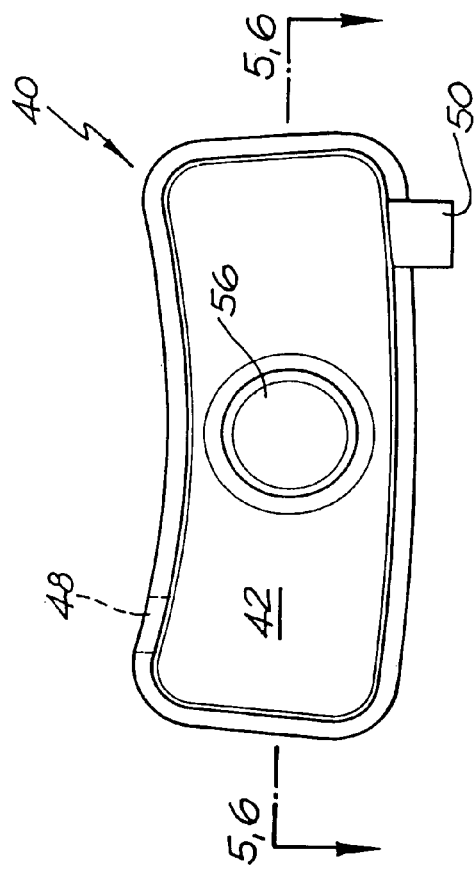
FIG. 3 is a top view of the humidifier shown in FIG. 2.

A second embodiment of a humidifier 40 is shown in FIGS. 2 to 9. As best shown in FIGS. 2 to 4, the humidifier 40 includes a hollow body formed from an upper body portion 42 and a lower body portion 44. A fluid tight seal 46 is disposed between the upper and lower body portions 42 and 44.

The upper body portion 42 includes a gas inlet 48 and a gas outlet 50.

Figure 5:
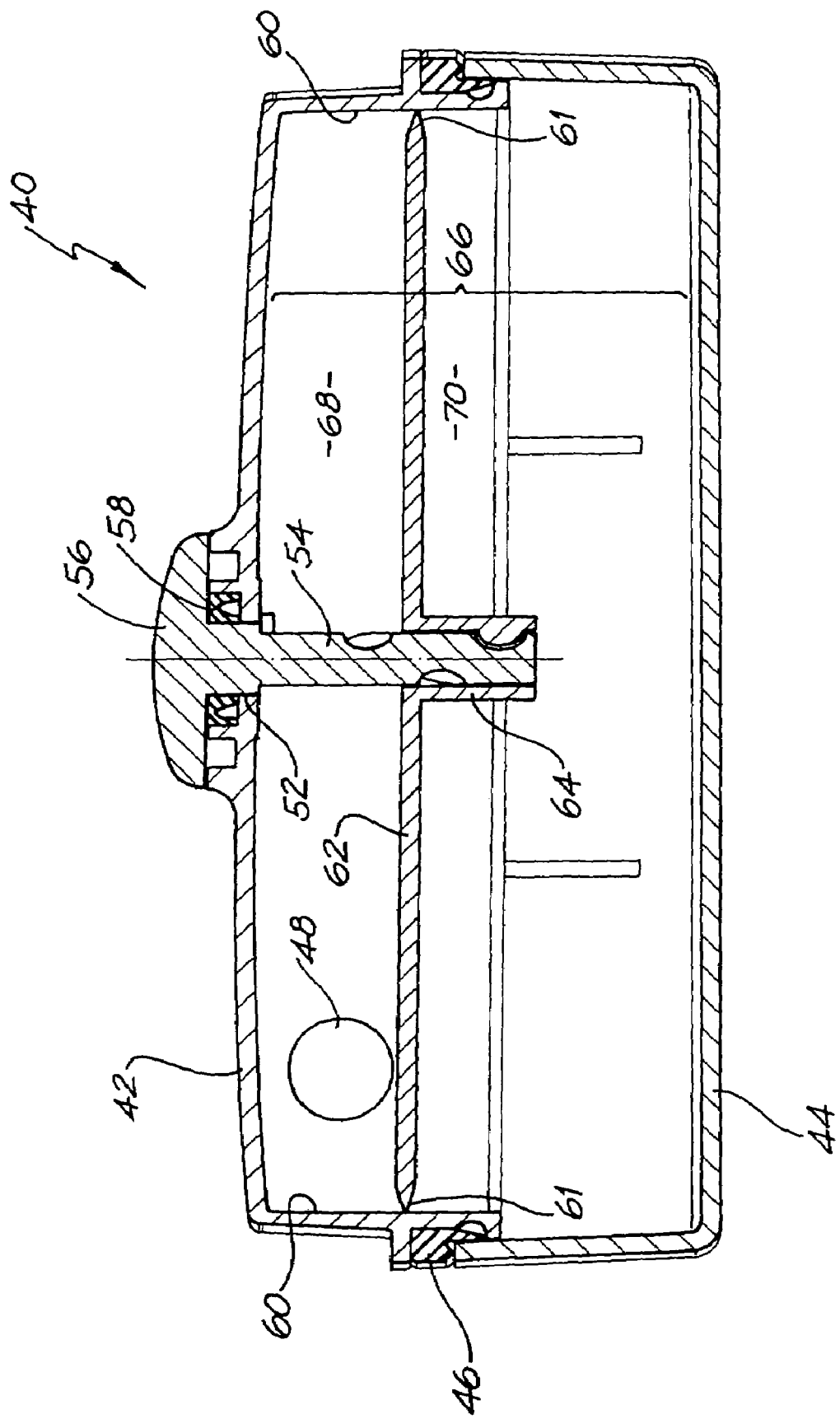
FIG. 5 is a partial cross sectional view along line 5,6—5,6 of FIG. 3 of the humidifier shown in FIG. 2 with the flow dividing plate in a minimum humidification position.

As best shown in FIG. 5, the upper body portion 42 also includes an opening 52 through which passes a threaded shaft 54. The shaft 54 depends from an external control knob 56.

A fluid tight seal 58 is provided around the shaft adjacent the knob 56 and the boss 52. The upper casing 42 includes substantially parallel internal side walls 60 which are adapted to provide a substantially fluid tight seal with the external edges 61 of a flow dividing plate 62. However, a fluid tight seal is not critical.

The plate 62 includes a central threaded boss 64 which threadably engages the shaft 54. Rotation of the knob 56 causes the boss 64, and thus the plate 62, to travel along the shaft 54 between the lower most position shown in FIG. 5 and upper most position shown in FIG. 6.

The lower body portion 44 is adapted to be filled with water to a level approximately 10 mm below the seal 46. When connected to a breathable gas supply apparatus, the humidifier 40 is positioned directly above a heating element which heats the water and causes water vapour to rise from the upper surface thereof. The upper body portion 42 and lower casing 44 together define the boundaries of the interior 66 of the humidifier 40. The plate 62 affectively divides the interior 66 above the water surface into a relatively dry gas region 68 above the plate 62 and a relatively wet gas region 70 below the plate 62.

When the knob 56 is rotated to position the plate 62 in the lowermost position shown in FIG. 5, the gas (normally air) pumped from the flow generator the inlet 48 of the humidifier 40 passes only through the dry region 68 and therefore undergoes minimal or zero humidification.

Figure 6:
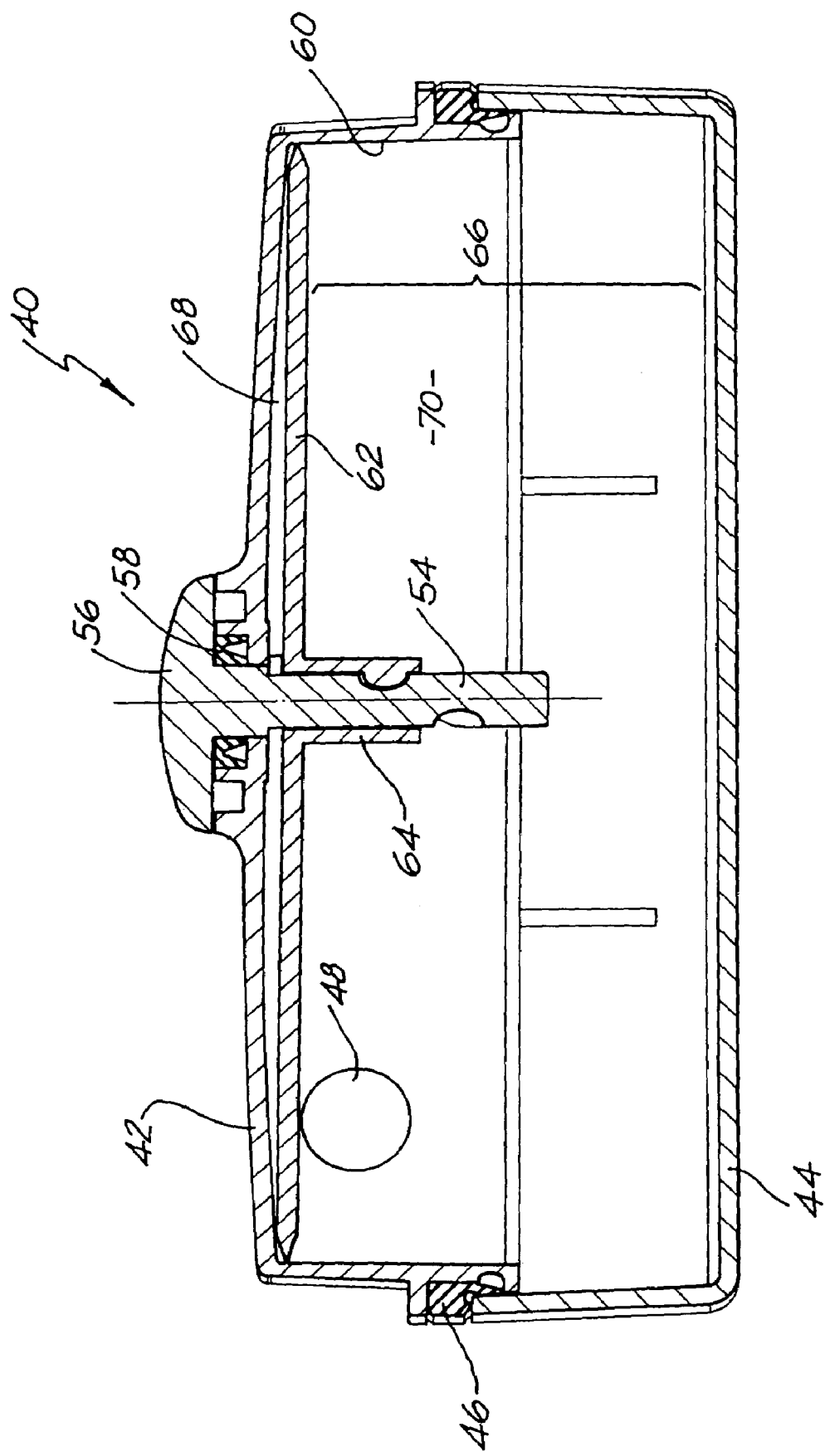
FIG. 6 is a partial cross sectional view along line 5,6—5,6 of FIG. 3 of the humidifier shown in FIG. 2 with the flow dividing plate in a maximum humidification position.

When the knob 56 is rotated to position the plate 62 in the uppermost position shown in FIG. 6, the gas passes only through the wet region 70 and therefore undergoes maximum humidification.

When the knob 56 is rotated to position the plate 62 intermediate the lowermost and uppermost position shown in FIGS. 5 and 6 respectively, then some of the supplied gas passes through the dry gas region 68 (and is not humidified) and some of the gas passes through the wet gas region 70 (and is humidified), which results in partial humidification overall. In this way, the adjustable plate 62 advantageously allows the amount of humidification of the supplied gas to be quickly and easily varied to suit individual user needs, comfort requirements, treatment regimes and changing atmospheric conditions.

Figure 7:
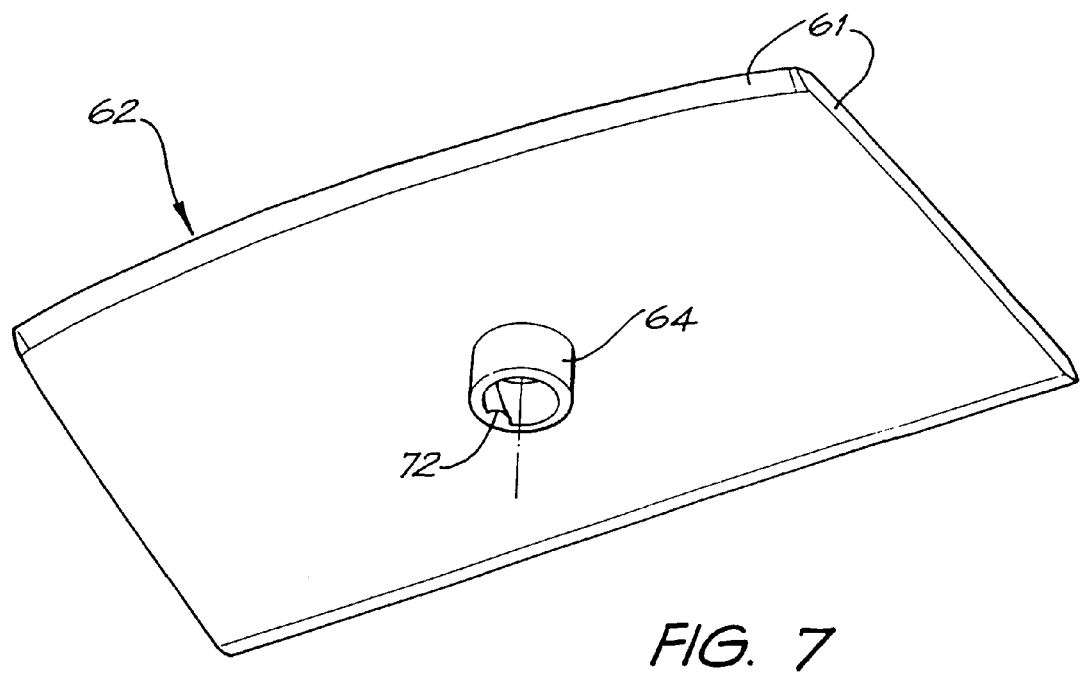
FIG. 7 is a lower perspective view of the flow divider of the humidifier shown in FIG. 2.
Figure 8:
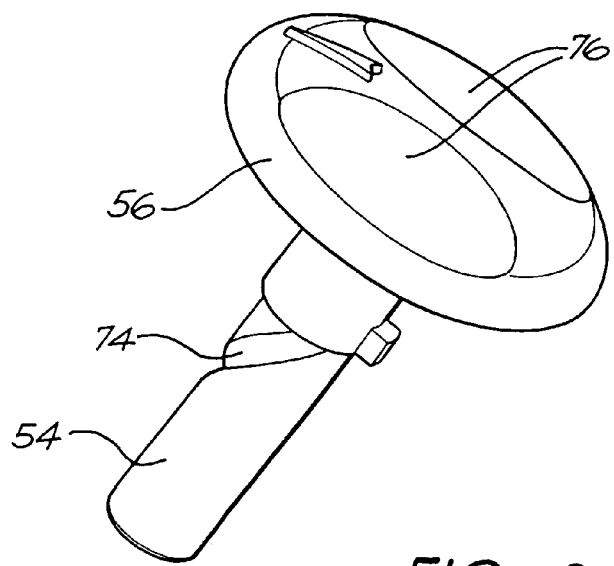
FIG. 8 is an upper perspective view of the control knob of the humidifier shown in FIG. 2.

The plate 62 is shown in isolation in FIG. 7 in which it can be seen that the boss 64 has a internal thread 72. The control knob 56 and shaft 54 are shown in isolation in FIG. 8 and it can be seen that the shaft 54 has an internal groove 74 which engages the thread 72 of the boss 64. The upper surface of the control knob 56 has two depressions 76 to facilitate gripping of the knob 56 by a user's fingers.

Figure 9:
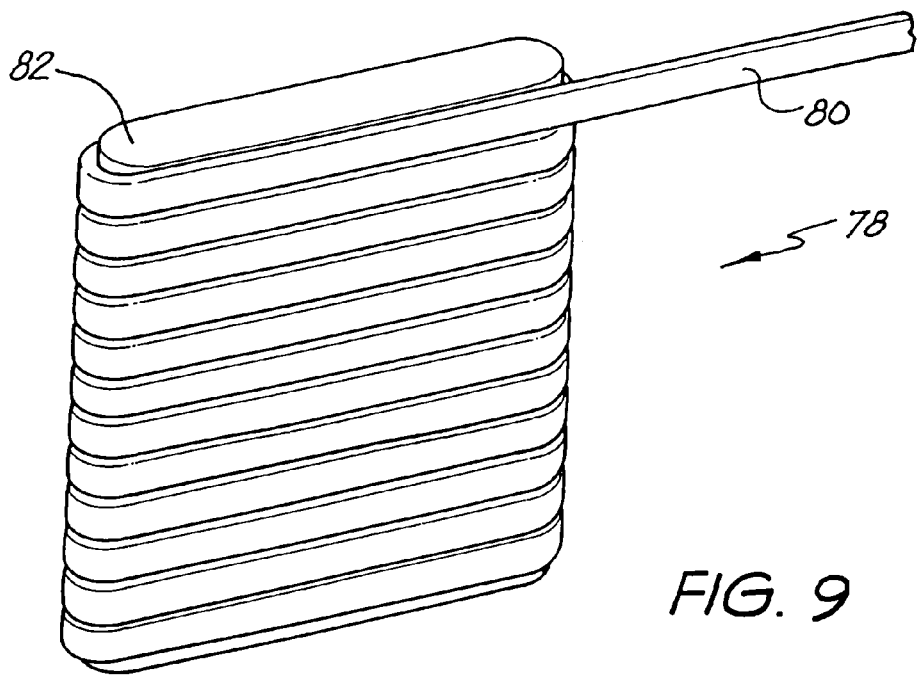
FIG. 9 is an upper perspective view of an embodiment of a heating element suitable for use with the humidifier shown in FIG. 2.

FIG. 9 shows a constant temperature heating element 78 suitable for use with the humidifier 40 shown in FIGS. 2 to 8. The heating element 78 comprises a length of self regulating wire 80, for example LSH-10, manufactured by Letco Products, Inc Texas (USA), which is wound around a core 82, for example Noryl, manufactured by General Electric. The self regulating wire 80 is able to be connected directly to mains power supply and, as mentioned above, advantageously obviates the need for thermostatic control equipment.

Figure 10:
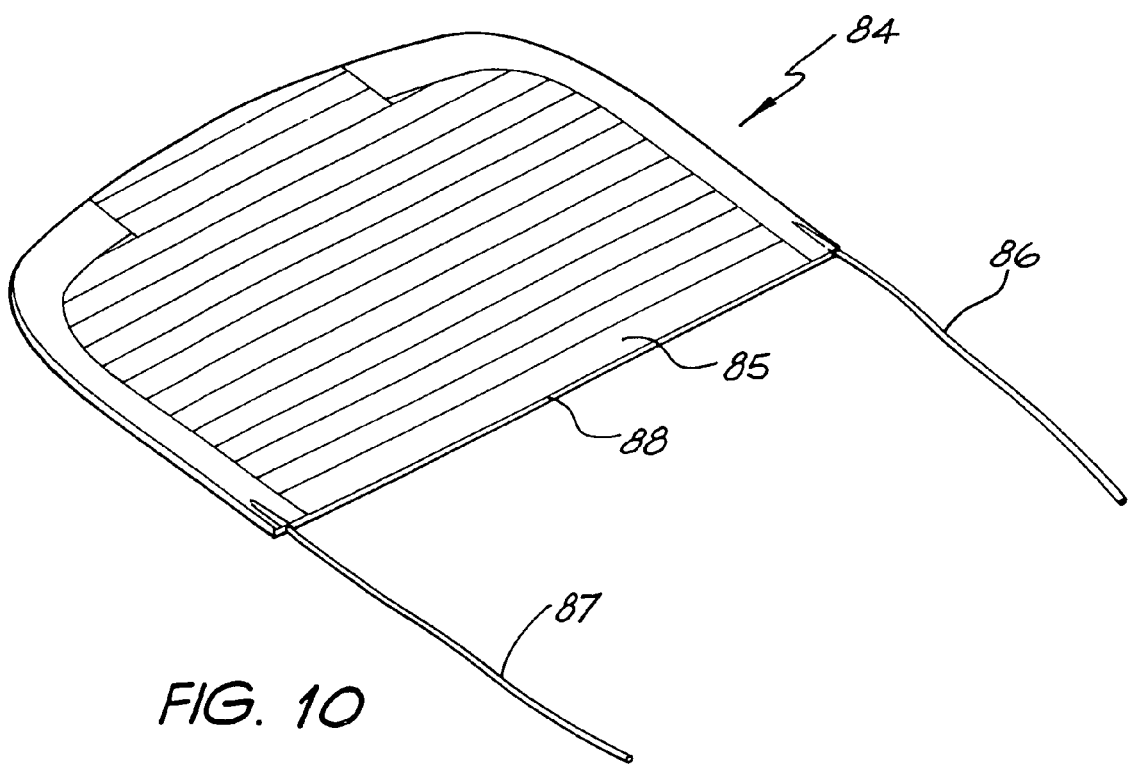
FIG. 10 is an upper perspective view of another embodiment of a heating element.

FIG. 10 shows another constant temperature heating element 84. The heating element 84 comprises a self regulating film 85 with power leads 86 and 87, for example manufactured by ITW, Illinios (USA), which is attached to a plate 88, for example Noryl.

Figure 11:
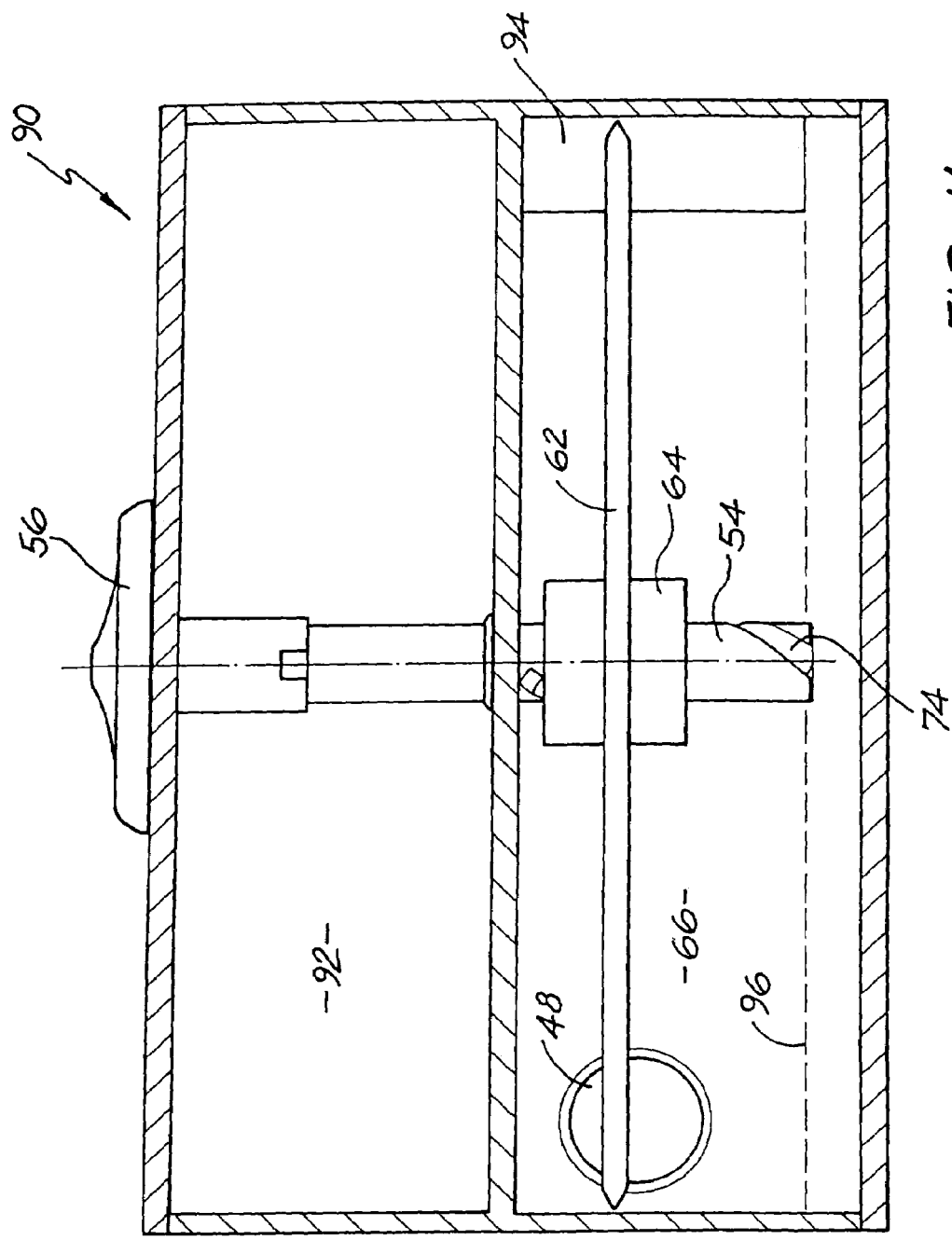
FIG. 11 is a cross sectional view of a humidifier according to a third embodiment of the invention.

FIG. 11 shows a third embodiment of a humidifier 90. Like reference numerals to those used in describing the second embodiment will be used to denote like features in the third embodiment.

The humidifier 90 has a water storage tank 92 positioned above the humidifier interior 66. A duct 94 allows water to flow from the tank 92 into the bottom of the interior 66 up to a maximum level indicated by dashed line 96. An additional advantage of this embodiment is that it can store a relatively large volume of water, to give a longer operational time between refilling, but it has a smaller volume of water adjacent the heating element, which reduces heating time and energy consumption.

Figure 12:
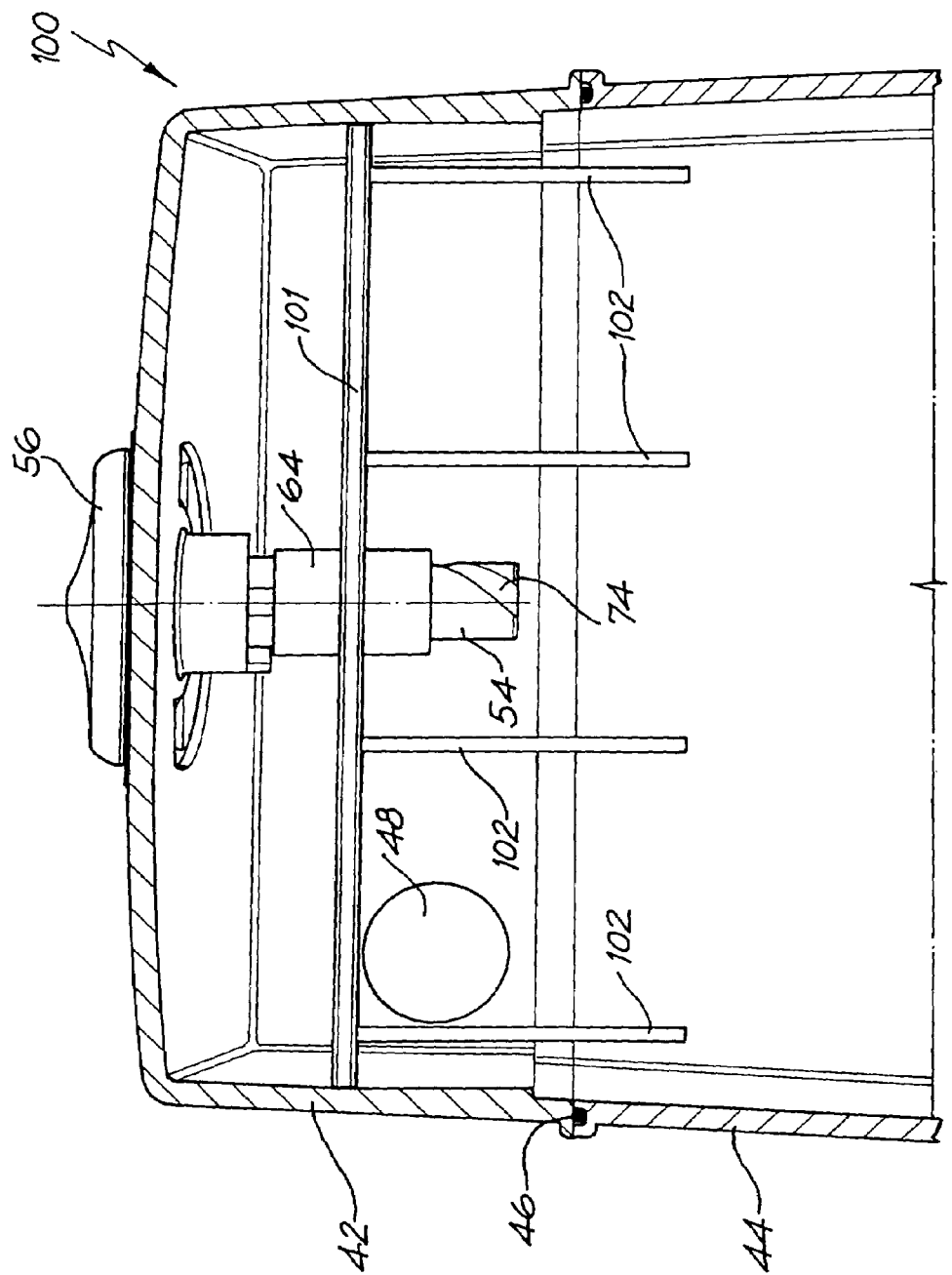
FIG. 12 is a partial cross sectional view of a humidifier according to a fourth embodiment of the invention.

FIG. 12 shows a fourth embodiment of the humidifier 100 according to the invention. Like reference numerals to those used in describing the second and third embodiments will again be used to denote like features.

The humidifier 100 is similar to the humidifier 40 shown in FIGS. 2 to 8 except it has a flow dividing plate 101 that includes four baffles 102. The baffles 102 cause the supplied gas to undertake a longer path between the humidifier inlet 48 and the outlet 50. An additional advantage of this embodiment is that it improves humidification by ensuring the supplied gas does not only flow over the portion of the water directly between the inlet 48 and outlet 50. A similar plate 101 is shown in FIG. 13, except that it includes eight of the baffles 102.

Figure 13:
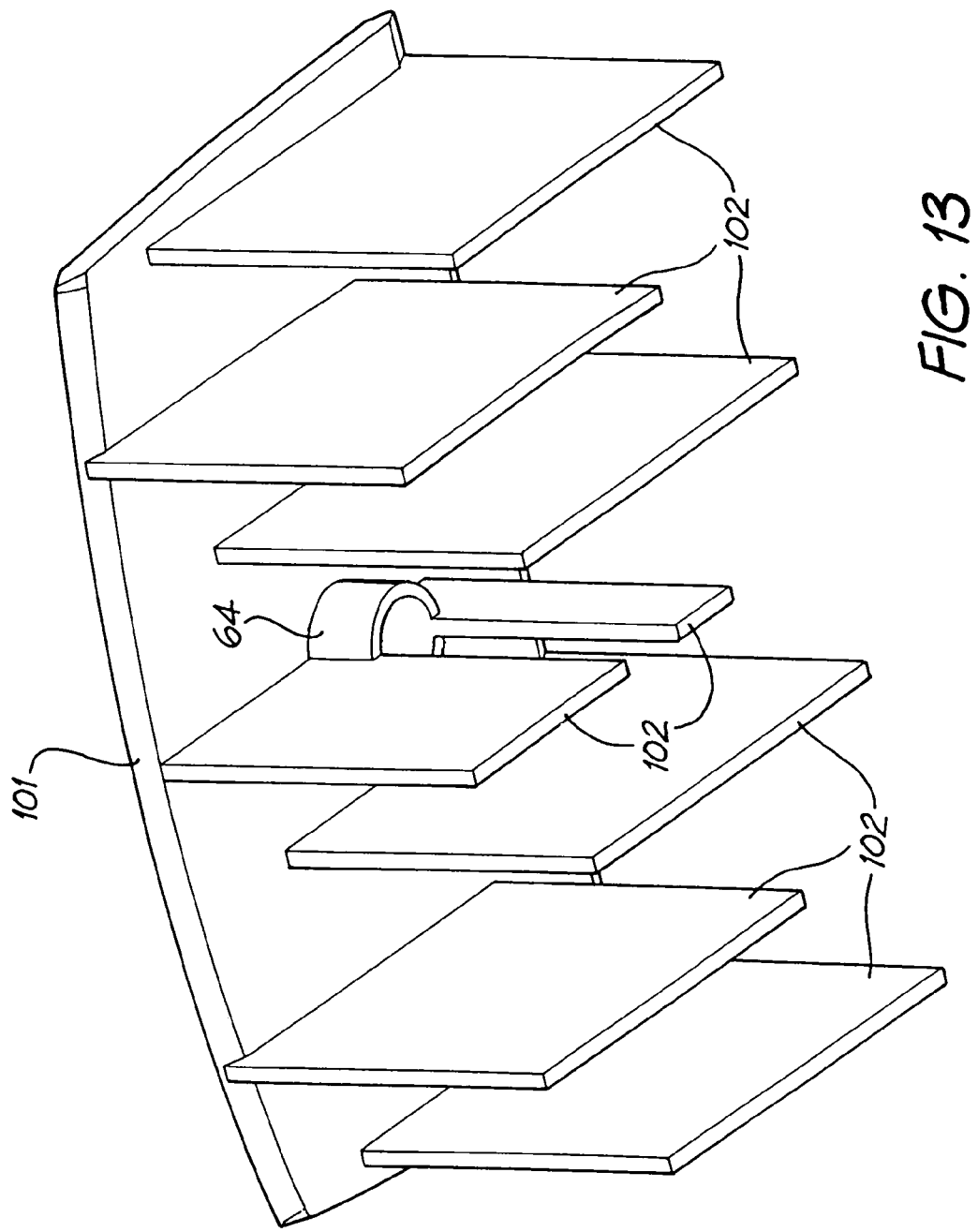
FIG. 13 is a lower perspective view of an embodiment of a flow dividing plate shown.

In the embodiments shown in FIGS. 12 and 13 the position of the baffles 102 are fixed. However, in other embodiments (not shown) the position of the baffles can be adjusted and/or individual baffles can be removed.

Figure 14:
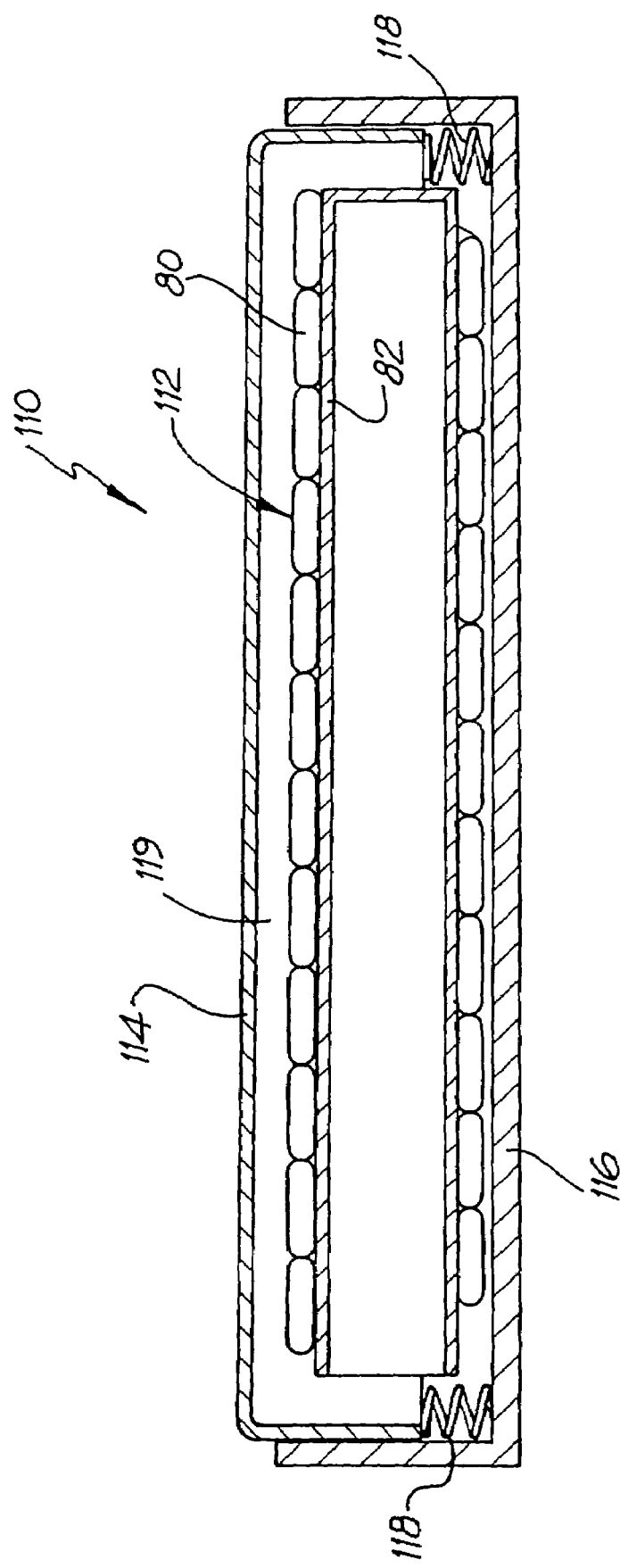
FIG. 14 is a cross sectional view of an embodiment of a heating element assembly.

FIG. 14 shows an embodiment of a heating element assembly 110 also suitable for use with humidifiers. The assembly 110 includes a heating element 112, which is similar to that shown in FIG. 9, and a heating plate 114. In use, the plate 114 is positioned between the upper surface of the heating element 112 and the lower surface or underside of a humidifier. The heating plate 114 is separated from a base 116 by springs 118.

When a humidifier filled with a predetermined volume (and thus weight) of water is placed on the heating plate 114, it compresses the springs 118 such that the plate 114 makes contact with the heating element 112 for heating. If there is insufficient water in the humidifier, or if the humidifier is removed from the assembly 110, the springs 118 lift the heating plate 114 away from the heating element 112. This creates an air gap 119 between the heating element 112 and the hot plate 114 which advantageously reduces further heating of the heating plate 114. This reduces the risk of the assembly 110 burning a user or starting a fire or the like if operated incorrectly.

Figure 15:
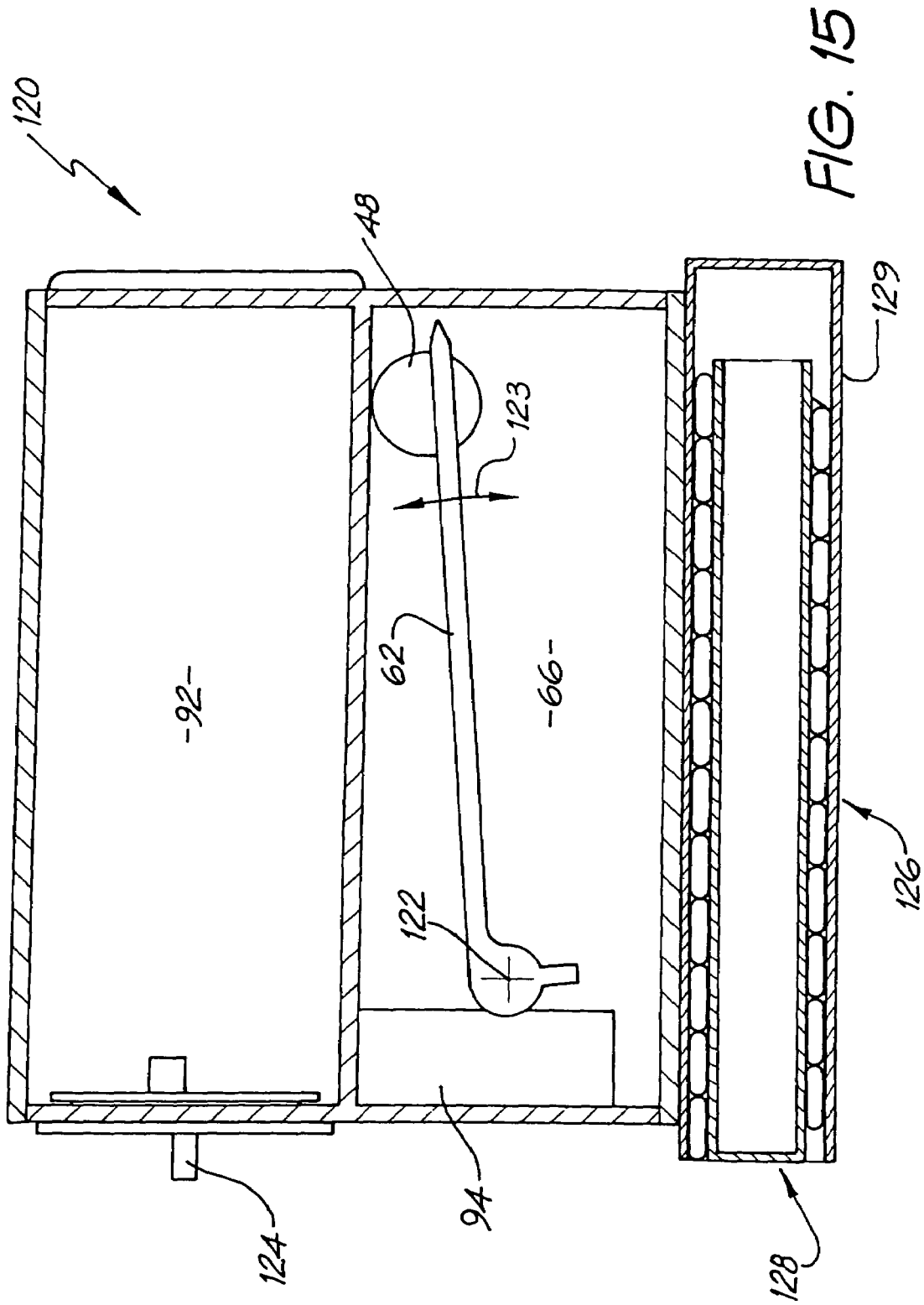
FIG. 15 is a cross sectional view of a humidifier according to a sixth embodiment of the invention.

FIG. 15 shows a humidifier 120 according to a sixth embodiment of the invention and like reference numerals will again be used to denote like features to earlier embodiments. The humidifier 120 is similar to the humidifier 90 shown in FIG. 11 in that it has a water storage tank 92 mounted above the humidification interior 66. However, in this embodiment, the flow dividing plate 62 pivots at one end about axis 122, as indicated by arrow 123, between maximum and minimum humidification positions. The humidifier 120 also includes a plug 124 to allow filling of the water storage tank 92. The humidifier 120 is shown mounted above a heating element assembly 126 which comprises a heating element 128 within an outer casing 129.

Figure 16:
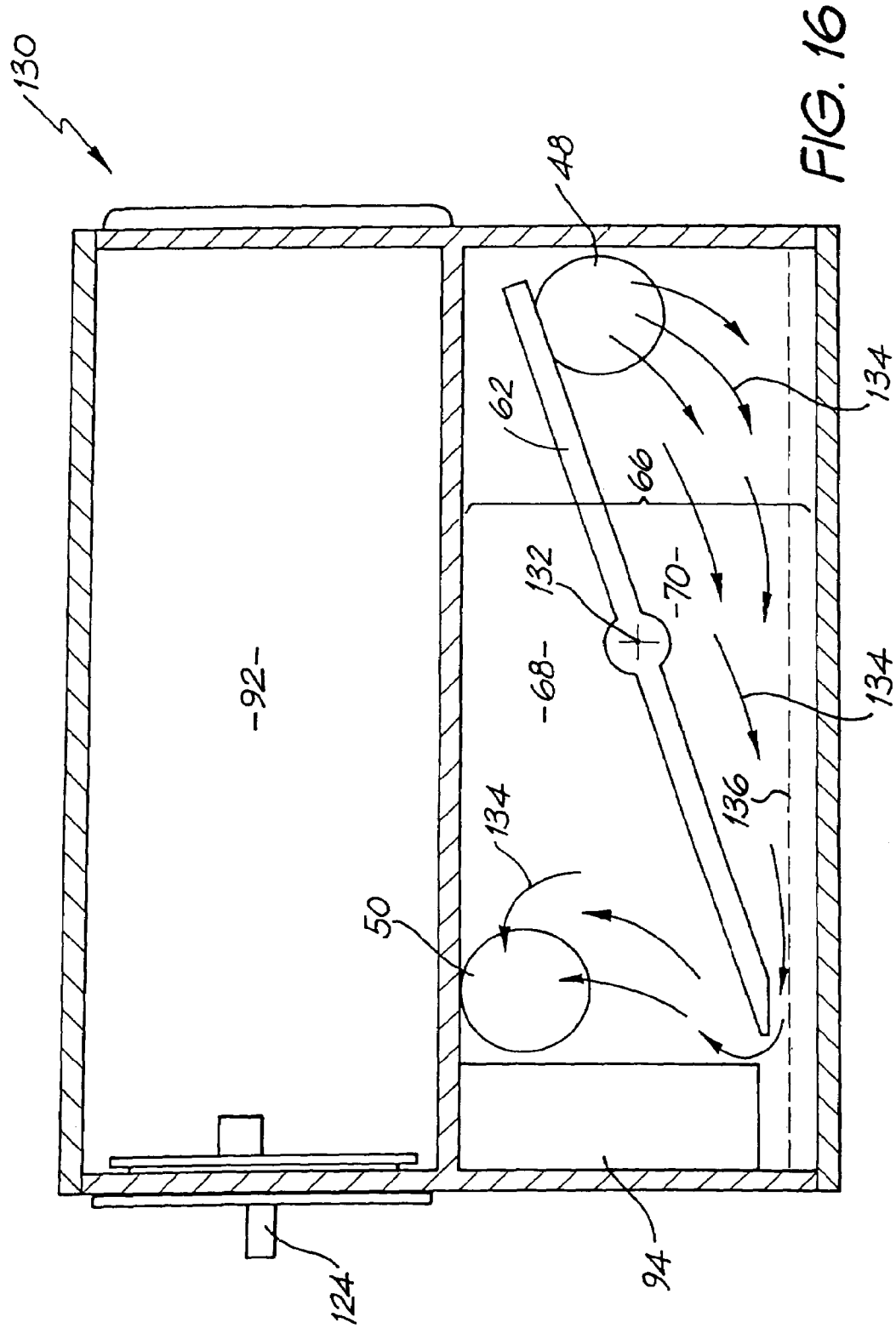
FIG. 16 is a cross sectional view of a humidifier according to a seventh embodiment of the invention with the flow dividing plate in a maximum humidification position.
Figure 17:
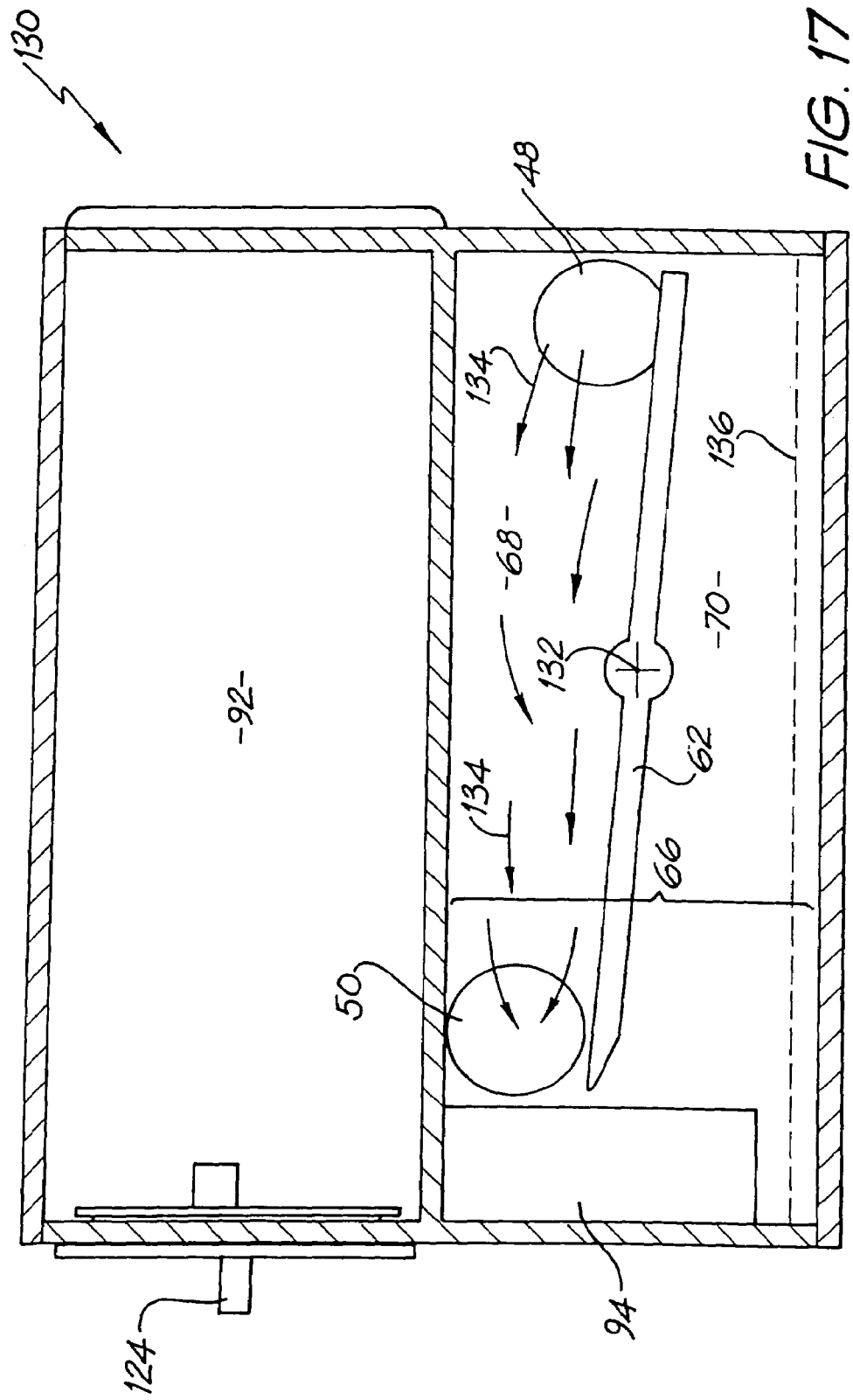
FIG. 17 is a cross sectional view of the humidifier of FIG. 15 with the flow dividing plate in a minimum humidification position.

FIGS. 16 and 17 show a seventh embodiment of a humidifier 130 similar to the embodiment shown in FIG. 15. However, in this embodiment, the flow dividing plate 62 rotates about a substantially central axis 132 between the maximum humidification position shown in FIG. 16 and the minimum humidification position shown in FIG. 17. The path taken by the supplied gas from the inlet 48 to the outlet 50 is indicated by arrows 134. The water level is indicated by broken line 136.

Figure 18:
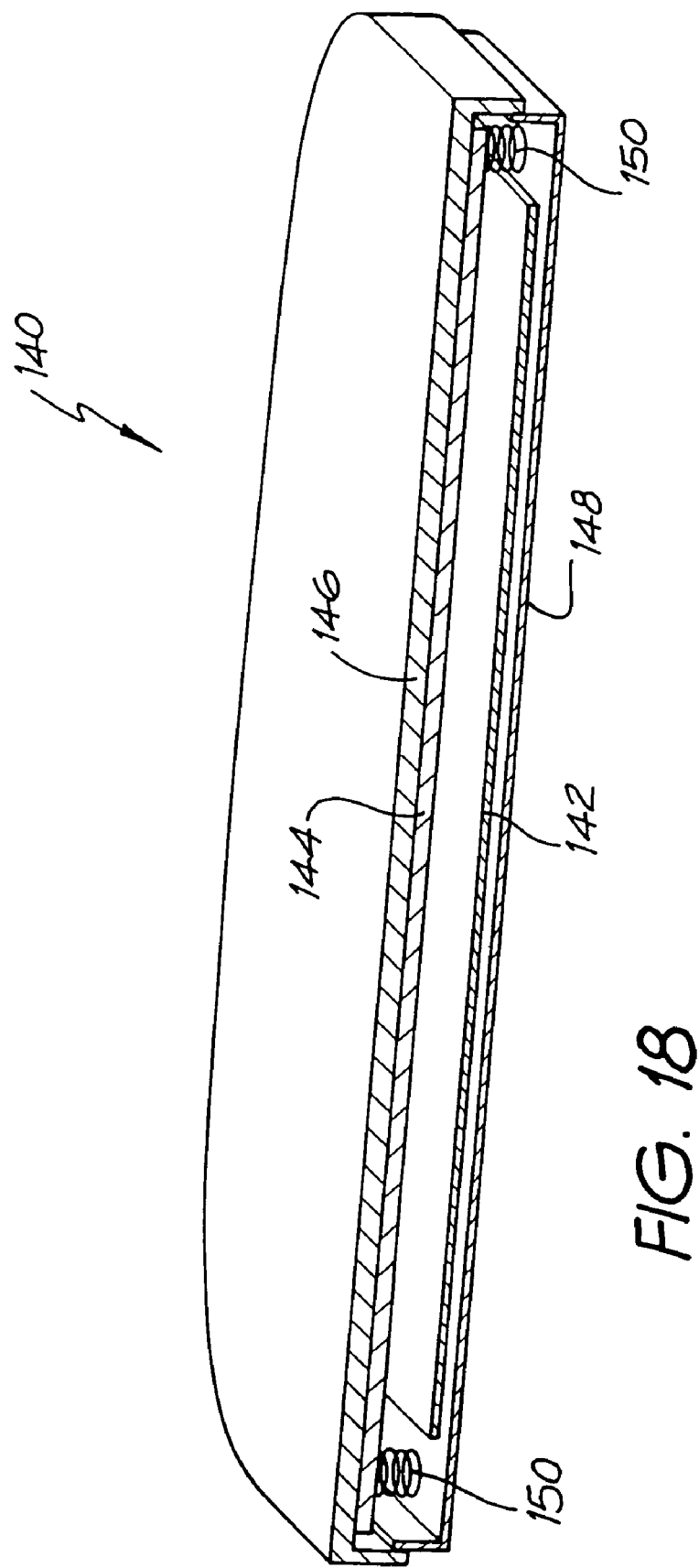
FIG. 18 is a cross sectional view of another embodiment of a heating element assembly.

FIG. 18 shows another embodiment of a heating element assembly 140 similar to that shown in FIG. 14. The assembly 140 includes a heating element 142, which is similar to that shown in FIG. 10, a conducting plate 144 and a heating plate 146. The heating plate 146 is separated from a base 148 by springs 150. The assembly 140 functions similar to the assembly 110 shown in FIG. 13.

Another advantage of the preferred embodiments of the invention stems from the ability to control humidification levels substantially independently of temperature. Different temperatures inhibit the growth of, or kill, different bacteria. For example, in chlorinated drinking water (0.2 mg/L) with a pH of 7.6, a temperature of 32 degrees C. will kill 99.9% of Legionel lapneumophilia in 30 minutes (VanDemark & Batzing (1987), The Microbes, Benjamin Cummings Publishing Company, Inc.). Accordingly, once a particular desired temperature has been identified, for example to effect a particular bacteria, a heating element can be manufactured to achieve that temperature. The desired effect will be achieved whenever the humidifier is operated with that element. The desired amount of humidification can be selected by adjusting the position of the flow dividing plate.

In contrast, with a thermostatically controlled humidifier, the above effect on bacteria could only be achieved by setting a minimum temperature in the thermostat. However, in the absence of other means to control the humidity, this limits the available range of humidification. For example, if the temperature could not be reduced below 40 degrees C., then a low range of humidification could not be achieved, unlike embodiments of the present invention.

Although the invention has been described with reference to specific examples, it is appreciated by those skilled in the art that the invention may be embodied in many other forms.

We claim:

1. A humidifier for use with a breathable gas supply apparatus, said humidifier comprising:

a hollow body adapted for at least partial filling with water to a predetermined maximum water level;

a gas inlet to the body above the maximum water level;

a gas outlet from the body above the maximum water level;

a heating element to heat the water in the body;

an adjustable flow divider adapted to divide the interior of the body above the maximum water level into a relatively dry gas region and a relatively wet gas region; and a filter operatively positioned at or near the gas inlet wherein the flow divider is adjustable to allow selective communication of the gas entering the body with the water in the body so that the gas entering the body can undergo zero added humidification, full added humidification, or partial added humidification.

2. A humidifier according to claim 1, wherein the filter is an antibacterial filter.

3. A humidifier according to claim 1, wherein the hollow body includes an upper body portion, a lower body portion, and a fluid tight seal between the upper and lower body portions.

4. A humidifier according to claim 3, wherein the upper body portion includes the gas inlet and the gas outlet.

5. A humidifier according to claim 1, wherein the flow divider includes a flow dividing plate that divides the interior of the body above the maximum water level into a relatively dry gas region above the plate and a relatively wet gas region below the plate.

6. A humidifier according to claim 1, wherein the flow divider is adjustable to a zero added humidification position that prevents communication of the gas entering the body at the gas inlet with the water in the body so that the gas passes through the relatively dry gas region of the body only.

7. A humidifier according to claim 1, wherein the flow divider is adapted to divide gas entering the body at the gas inlet into the relatively dry gas region and the relatively wet gas region.

8. A humidifier according to claim 1, wherein the flow divider is adjustable to allow relatively dry gas to pass from the gas inlet to the gas outlet through the interior of the body.

9. A humidifier according to claim 1, wherein the flow divider is adjustable to control a volume of gas that passes over the water within the hollow body.

10. A humidifier according to claim 1, wherein the flow divider is adapted to divide the interior of the body into an air flow path for relatively dry gas and an air flow path for relatively wet gas.

11. A humidifier according to claim 1, wherein the flow divider is positioned in covering relation with respect to the water in the body.

12. A humidifier according to claim 1, wherein the flow divider is substantially parallel to and substantially equal in length compared to top and bottom walls of the body.

13. A humidifier according to claim 1, wherein the flow divider is adjustable to allow (1) gas to pass from the gas inlet to the gas outlet through a first air flow passage in which gas undergoes zero added humidification, (2) gas to pass from the gas inlet to the gas outlet through a second air flow passage in which gas undergoes full added humidification, and (3) gas to pass from the gas inlet to the gas outlet through both the first and second air flow passages in which gas undergoes partial added humidification.

14. A humidifier according to claim 1, wherein gas is delivered to the relatively dry gas region of the body at the gas inlet.

15. A humidifier according to claim 1, wherein the gas inlet includes a gas inlet orifice such that the filter is operatively positioned near the gas inlet orifice of the gas inlet.

16. A humidifier for use with a breathable gas supply apparatus, said humidifier comprising:

a hollow body adapted for at least partial filling with water to a predetermined maximum water level;

a gas inlet to the body above the maximum water level;

a gas outlet from the body above the maximum water level;

a heating element to heat the water in the body;

an adjustable flow divider adapted to divide the interior of the body above the maximum water level into a relatively dry gas region and a relatively wet gas region; and a filter operatively positioned at or near the gas inlet, wherein the filter extends along a length of the body.

17. A humidifier according to claim 16, wherein the filter has a length that is substantially the same as the length of the body.

18. A breathable gas supply apparatus for CPAP or NIPPV treatment including the humidifier according to claim 1.

19. A breathable gas supply apparatus according to claim 18, wherein the apparatus is constructed to deliver to the humidifier gas pressurized in the range of 4–20 cmH$_2$O.

20. A breathable gas supply apparatus, comprising:
a flow generator with a gas outlet; and
the humidifier according to claim 1,
wherein the filter is operatively positioned between the gas outlet of the flow generator and the gas inlet of the humidifier.

21. A breathable gas supply apparatus, comprising:
a flow generator including a blower; and
the humidifier according to claim 1,
wherein the blower is positioned before the gas inlet of the humidifier such that gas is adapted to pass through the blower before passing through the gas inlet of the humidifier.

22. A humidifier for use with a breathable gas supply apparatus, said humidifier comprising:
a hollow body adapted for at least partial filling with water;
a gas inlet provided to the body;
a gas outlet provided to the body; and
an adjustable flow divider adapted to divide gas entering an interior of the body at the gas inlet into a relatively dry gas region in the body and a relatively wet gas region in the body,
wherein the body, inlet, outlet, and divider are structured to combine relatively dry gas from the relatively dry gas region and relatively wet gas from the relatively wet gas region for delivery of the gas at a predetermined humidity level through the gas outlet of the body.

23. A breathable gas supply apparatus for CPAP or NIPPV treatment including the humidifier according to claim 16.

24. A breathable gas supply apparatus according to claim 23, wherein the apparatus is constructed to deliver to the humidifier gas pressurized in the range of 4–20 cmH$_2$O.

25. A breathable gas supply apparatus, comprising:
a flow generator with a gas outlet; and
the humidifier according to claim 16,
wherein the filter is operatively positioned between the gas outlet of the flow generator and the gas inlet of the humidifier.

26. A breathable gas supply apparatus, comprising:
a flow generator including a blower; and
the humidifier according to claim 16,
wherein the blower is positioned before the gas inlet of the humidifier such that gas is adapted to pass through the blower before passing through the gas inlet of the humidifier.

27. A breathable gas supply apparatus for CPAP or NIPPV treatment including the humidifier according to claim 22.

28. A breathable gas supply apparatus according to claim 27, wherein the apparatus is constructed to deliver to the humidifier gas pressurized in the range of 4–20 cmH$_2$O.

29. A breathable gas supply apparatus, comprising:
a flow generator with a gas outlet;
the humidifier according to claim 22; and
a filter operatively positioned between the gas outlet of the flow generator and the gas inlet of the humidifier.

30. A breathable gas supply apparatus, comprising:
a flow generator including a blower; and
the humidifier according to claim 22,
wherein the blower is positioned before the gas inlet of the humidifier such that gas is adapted to pass through the blower before passing through the gas inlet of the humidifier.

* * * * *